United States Patent
Rodriguez et al.

(10) Patent No.: US 9,422,579 B2
(45) Date of Patent: Aug. 23, 2016

(54) METHOD FOR CONVERSION OF HALOPHYTIC BIOMASS TO BIOGAS VIA THALASSIC ANAEROBIC DIGESTION

(71) Applicant: Masdar Institute of Science and Technology, Abu Dhabi (AE)

(72) Inventors: Jorge Rodriguez, Abu Dhabi (AE); Joao Marcus Uratani, Abu Dhabi (AE)

(73) Assignee: Masdar Institute of Science and Technology, Abu Dhabi (AE)

( * ) Notice: Subject to any disclaimer, the term of this patent is extended or adjusted under 35 U.S.C. 154(b) by 0 days.

(21) Appl. No.: 14/314,685

(22) Filed: Jun. 25, 2014

(65) Prior Publication Data
US 2014/0377828 A1 Dec. 25, 2014

Related U.S. Application Data

(60) Provisional application No. 61/839,198, filed on Jun. 25, 2013.

(51) Int. Cl.
*C12P 5/02* (2006.01)
*C10L 1/02* (2006.01)

(52) U.S. Cl.
CPC .............. *C12P 5/023* (2013.01); *C10L 1/026* (2013.01); *Y02E 50/343* (2013.01)

(58) Field of Classification Search
None
See application file for complete search history.

(56) References Cited

U.S. PATENT DOCUMENTS

| 4,975,106 A | 12/1990 | Ferguson |
| 5,055,406 A * | 10/1991 | Nakatsugawa et al. ..... 435/252.1 |
| 2005/0048080 A1* | 3/2005 | Katzen ..................... 424/195.17 |
| 2011/0039321 A1 | 2/2011 | Tal et al. |

FOREIGN PATENT DOCUMENTS

| EP | 2283108 | 11/2009 |
| KR | 20110055795 A | 5/2011 |

OTHER PUBLICATIONS

Akinshina "Anaerobic Degradation of Halophyte Biomass for Biogas Production" Journal of Arid Land Studies, 22-1, 227-230, May 24-28, 2012.*
Riffat "Anaerobic Treatment of High-Saline Wastewater Using Halophilic Methanogens in Laboratory-Scale Anaerobic Filters", Water Environment Research, vol. 79, No. 2, 2007 191-1998.*
Lu "Nutritional characterization and changes in quality of *Salicornia bigelovii* Torr. during storage" LWT—Food Science and Technology, 43 (2010) 519-524.*
Pickleweed, Westminster College, available at people.westminstercollege.edu/faculty/tharrison/gslplaya99/pickleweed.htm, accessed on Jul. 7, 2015.*

(Continued)

*Primary Examiner* — Robert Yamasaki
*Assistant Examiner* — Charles Zoltan Constantine
(74) *Attorney, Agent, or Firm* — Myers Bigel & Sibley, P.A.

(57) ABSTRACT

Described is a process for the conversion of halophytic plant biomass containing saline organic solids into biogas through anaerobic digestion. Operation of the process with saline (e.g., seawater) as liquid media under the method conditions taught leads to biological conversion of the organic matter into biogas. Additionally described is a method for pretreatment of the biomass under mild physicochemical conditions to increase the bioavailable fraction of the biomass for conversion.

19 Claims, 1 Drawing Sheet

(56) References Cited

OTHER PUBLICATIONS

Christiansen, "Sea asparagus can be oil feedstock" Biodiesel Magazine, Jul. 2008.*
Paterek "Isolation and Characterization of a Halophilic Methanogen from Great Salt Lake" Applied and Environmental Microbiology, Oct 1985, p. 877-881.*
Swain "Environmental Aspects of Marsh Gases" Available at www.caer.uky.edu/publications/gsapub7/Swain.pdf, and available since Nov. 4, 2004 as recorded by wayback web archive web.archive.org/web/20041104085432/http://www.caer.uky.edu/publications/gsapub7/Swain.pdf.*
Seawater Properties Rhode Island College, OC202 Topic 1: Seawater Properties, available at www.ric.edu/faculty/PSCI103/Seawater/Seawater_notes.htm, accessed Jul. 7, 2015.*
*Salicornia bigelovii*. Wikipedia. Jun. 21, 2013: 2 pp. http://en.wikipedia.org/wiki/Salicornia_bigelovii.
Halophyte. Wikipedia. Jun. 21, 2013: 2 pp. https://en.wikipedia.org/wiki/Halophyte.
Marquez GPB et al. Thalassic biogas production from sea wrack biomass using different microbial seeds: cow manure, marine sediments and sea wrack-associated microflora. Bioresourse Technology. Apr. 2013; 133: 612-617. Abstract only.
Akinshina N et al. Anaerobic degradation of halophyte biomass for biogas production. Journal of Arid Land Studies. 2012; 22-1: 227-230.
Taha F et al. Promoting sustainable renewable energy production on marginal lands of Central Asia. 14th Steering Committee Meeting of the CGIAR Eco-Regional Collaborative Research Program for Central Asia and the Caucasus. Sep. 20-22, 2013. International Business Center, Tashkent, Uzbekistan. 10 pp.

* cited by examiner

METHOD FOR CONVERSION OF HALOPHYTIC BIOMASS TO BIOGAS VIA THALASSIC ANAEROBIC DIGESTION

BACKGROUND

Biofuel production using land crops has been under criticism due to environmental and economic shortcomings. The main criticisms are land usage competition, utilization of food crops as feedstock, large fresh water demand for irrigation and low energy production yields (Escobar et al., 2008; Stoeglehner and Narodoslawsky 2009; Börjesson and Tufvesson, 2011). Several alternatives that address these negative impacts have been proposed (Brennan and Owende, 2010; Naik et al., 2010). However, better options for producing biofuels are needed.

BRIEF SUMMARY OF EMBODIMENTS

Provided herein are methods for producing a biofuel (e.g., a biogas such as methane) from a halophyte substrate comprising providing a composition comprising said substrate in a saline medium. In some embodiments, the method includes adding a culture comprising halophilic microbes (e.g., anaerobic archaea) to said composition in an amount effective to digest said halophyte; and then, digesting said substrate with said culture for a time sufficient to produce a biofuel therefrom.

In some embodiments, the saline medium has a salt concentration of from about 30 g/L to about 60 g/L $NaCl_{eq}$.

In some embodiments, the digesting is carried out in batch mode, fed-batch mode, continuous mode, or sequential batch reactors.

In some embodiments, the halophyte is a *Salicornia* species (e.g., *Salicornia bigelovii*).

In some embodiments, the halophyte substrate is deseeded. In some embodiments, the halophyte substrate consists essentially of shoots, stems, and/or roots of said halophyte.

In some embodiments, the method may further include pretreating the halophyte substrate prior to the providing step, including hydrolysis of said substrate. In some embodiments, the hydrolysis is carried out in a saline solution. In some embodiments, the saline solution of said pretreating step has a salinity concentration of from about 30 to about 60 g NaCl/L. In some embodiments, the saline solution of said pretreating step comprises, consists of or consists essentially of seawater.

In some embodiments, the culture comprising halophilic microbes is from a wastewater treatment plant, a marine soil sediment, a mangrove sediment, or from a combination thereof.

In some embodiments, the culture is adapted, e.g., by prior cycling with the substrate and/or saline medium in a batch reactor.

In some embodiments, the saline medium comprises, consists of or consists essentially of seawater, saline waste water, or a combination thereof.

Also provided is a method of producing biofuels from a halophyte plant, including growing said plant in a saline medium, wherein said plant comprises shoots, stems, roots and seeds; harvesting the seeds of said plant, wherein said harvesting is carried out by separating said seeds from said shoots, stems and roots, said remaining shoots, stems and roots forming a halophyte substrate; and then digesting the halophyte substrate to produce a biofuel, wherein said biofuel is produced according to the methods taught herein.

DETAILED DESCRIPTION OF EMBODIMENTS

Figure 1:
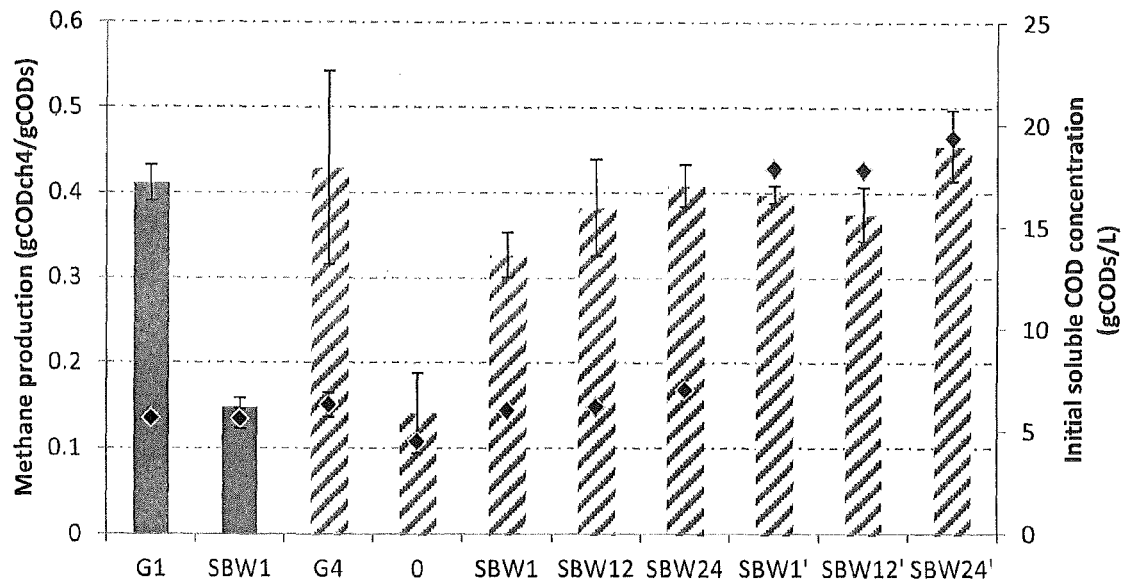
FIG. 1 shows the cumulative total methane production (from gas volume and composition) after 14-day of batch (dark grey bars), initial soluble COD concentration (black diamonds), and the cumulative total methane production after 30 days with fourth cycle adapted inoculum (grey diagonal striped bars). G1 and G4 are triplicates with glucose as sole COD source; SBW# are triplicates with SBW-ES as sole COD source; # denotes the extraction time (1, 12 or 24 hours). 0 are control triplicates with no carbon source. Negative controls containing only media and SBW were also cultivated (not shown) with negligible methane production.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

The term "about" as used herein when referring to a measurable value such as an amount or concentration (e.g., salinity) and the like, is meant to encompass variations of ±20%, ±10%, ±5%, ±1%, ±0.5%, or even ±0.1% of the specified amount or value.

The term "consist essentially of", as used herein in reference to a saline solution (such as seawater), is meant that at least 80%, such as 90, 95 or 99 percent, is made up of such saline by weight or by volume.

The present inventors have found that halophytic plant biomass can be efficiently degraded to biofuel with only a mild pretreatment. Typical plant biomass, by contrast, is rich in lignin and cellulosic materials, which limit bioconversion in the absence of a severe pretreatment. In some embodiments, the AD was accomplished with only mild conditions in pre-treatment of the substrate (e.g., at temperatures of about 50 degrees Celsius), as opposed to traditional pre-treatment processes involving high temperature and/or addition of enzymes for hydrolysis. Mild pretreatment may include, but is not limited to, one or more of: drying, grinding (course or fine), extraction in a saline medium (e.g., 1, 2, 5, 10 or 15% dry weight per volume (dw/v)) for from 1 to 40 hours (e.g., at a temperature of from 30 or 35 to 45, 50, 75 or 95° C.), which may be followed by centrifugation.

In addition, the inventors have found that anaerobic digestion (AD) of the halophytic plant biomass can be achieved in saline solution, without the need for fresh water in the process. Conventional AD processes are known to be inhibited by higher values of salinity concentration in medium.

The methane produced is also notably of high quality, with low concentrations of hydrogen sulfide gas. Hydrogen sulfide is produced by anaerobic sulfur-reducing bacteria, which compete with methanogens for the energy course (as COD) in the AD bioreactor. In some embodiments, the methane biogas contains less than 5%, 3%, 1%, or 0.5% of hydrogen sulfide (v/v).

A "halophyte" is a plant that can grow in waters of high salinity, such as seashores, marshes, sloughs, saline semi-deserts, and mangrove swamps. Relatively few plant species are halophytes. Most plants, by contrast, are glycophytes and are very sensitive and easily damaged by salinity. Halophytes of interest include, but are not limited to, species of *Climacoptera* (e.g., *Climacoptera lanata*), *Kalidium* (e.g., *Kalidium caspicum*), *Kosteletzkya* (e.g., *Kosteletzkya virginica*), *Panicum* (e.g., *Panicum coloratura*), *Salicornia* (e.g., *Salicornia bigelovii, Salicornia europea*), *Sarcocornia*, *Spartina* (e.g., *Spartina alterniflora*), *Suaeda* (e.g., *Suaeda salsa*), and *Tamarix*. The halophyte "substrate" includes halophyte plant parts, such as stems and branches, which may optionally be subjected to pretreatment before digestion as taught herein.

*Salicornia* species are halophytes found in coastal environments (e.g., salt marshes, mangroves) in most continents. The members of this genus use the C4 pathway for carbon fixation (Hatch-Slack pathway), using atmospheric $CO_2$ as the carbon source (Bassam, 2010). Differences in hemicellulose major polymers and monomeric composition are observed when compared to non-halophytic plant extracts (such as sugar beet, also a member in the former Chenopodiaceae family, currently included in the Amaranthaceae family).

*Salicornia* is capable of growing under immersion in salt water, tolerating up to 60 g/L of $NaCl_{eq}$ salt concentration in irrigation water (Silva et al., 2007). This crop does not need fresh water for irrigation, but also can be cultivated in non-arable saline land, as found in many coastal areas in the Arabian Gulf. Growth under irrigation with high-salinity water can be promoted with inoculation of plants with halo-tolerant, nitrogen-fixing bacteria, which increases the biomass dry weight without a corresponding increase in seed dry weight.

The seeds of *Salicornia*, such as *S. bigelovii*, are of interest as an oil crop for biodiesel production, due to their high-lipid low lignocellulose content (Glenn et al., 1991), and also for animal feed from the seed waste from the oil extraction, called *salicornia* meal (SM) (Glenn et al., 1992). Production of vegetable salt from the juice of the plant has also been proposed. See KR 20110055795. See also WO 2013017289 to Ernst et al.; EP 2602306 to Warnqvist.

Dried stems, branches and deseeded inflorescences compose the *salicornia* biomass waste (SBW), from which concentrations of soluble COD up to 0.305 gCODs/g dry matter are easily obtained under very mild aqueous extraction with ammoniacal nitrogen concentrations of the extractive remaining below biomethanisation inhibitory levels (Chaturvedi et al., 2013).

"Chemical oxygen demand" or "COD" is a measurement of the energy that a microorganism can utilize for growth and bioprocessing. This, in turn can predict biofuel production capacity.

"Ammoniacal nitrogen" or "$NH_3$—N" is a known inhibitor of anaerobic digestion, along with salinity. In some embodiments of the invention, $NH_3$—H concentrations produced during digestion are below AD inhibitory levels.

In some embodiments of the invention, a culture comprising halophilic microorganisms is provided for one or more of the digestion steps, and may include halophilic bacteria and archaea provided in an amount effective to digest a halophyte substrate and/or produce a biogas from a halophyte substrate. Exemplary halophilic microorganisms are provided in Table 1

TABLE 1

| Halophillic Microorganisms |
|---|
| *Alkalibacillus filiformis* |
| *Alkalibacillus haloalkaliphilus* |
| *Alkalibacillus halophilus* |
| *Alkalibacillus salilacus* |
| *Alkalibacillus silvisoli* |
| *Allochromatium minutissimum* |
| *Allochromatium phaeobacterium* |
| *Allochromatium renukae* |
| *Allochromatium vinosum* |
| *Allochromatium warmingii* |
| *Amphibacillus fermentum* |
| *Amphibacillus tropicus* |
| *Amphibacillus xylanus* |
| *Anoxybacillus kamchatkensis asaccharedens* |
| *Arcobacter halophilus* |
| *Arcobacter nitrofigilis* |
| *Arcobacter sulfidicus* |
| *Bacillus aeolius* |
| *Bacillus alkalinitrilicus* |
| *Bacillus alkalitelluris* |
| *Bacillus amyloliquefaciens* |
| *Bacillus aquimaris* |
| *Bacillus bogoriensis* |
| *Bacillus cereus* |
| *Bacillus chagannorensis* |
| *Bacillus cohnii* |
| *Bacillus dipsosauri* |
| *Bacillus fumarioli* |
| *Bacillus galliciensis* |
| *Bacillus halodenitrificans* |
| *Bacillus halodurans* |
| *Bacillus horneckiae* |
| *Bacillus hwajinpoensis* |
| *Bacillus indicus* |
| *Bacillus infernus* |

TABLE 1-continued

Halophillic Microorganisms

*Bacillus isabeliae*
*Bacillus jeotgali*
*Bacillus licheniformis*
*Bacillus locisalis*
*Bacillus marisflavi*
*Bacillus marismortui*
*Bacillus megaterium*
*Bacillus mojavensis*
*Bacillus nanhaiisediminis*
*Bacillus neizhouensis*
*Bacillus oceanisediminis*
*Bacillus oleronius*
*Bacillus pallidus*
*Bacillus persepolensis*
*Bacillus polymyxa*
*Bacillus pseudofirmus*
*Bacillus pumilus*
*Bacillus qingdaonensis*
*Bacillus rigui*
*Bacillus salarius*
*Bacillus salexigens*
*Bacillus selenitireducens*
*Bacillus smithii*
*Bacillus sporothermodurans*
*Bacillus subtilis*
*Bacillus taeanensis*
*Bacillus thioparus*
*Bacillus vedderi*
*Cerasibacillus quisquiliarum*
*Cerasicoccus frondis*
*Cerasicoccus maritimus*
*Chromohalobacter marismortui*
*Chromohalobacter* sp.
*Desulfovibrio capillatus*
*Desulfovibrio gabonensis*
*Desulfovibrio portus*
*Desulfovibrio profundus*
*Dunaliella bardawil*
*Dunaliella salina*
*Dunaliella* sp.
*Ectothiorhodosinus mongolicum*
*Ectothiorhodospira salini*
*Filobacillus milensis*
*Frauteria aurentia*
*Geobacillus thermoleovorans*
*Geobacillus teobii*
*Geobacillus* sp.
*Geomicrobium halophilum*
*Gracilibacillus halophilus*
*Gracilibacillus halotolerans*
*Gracilibacillus orientalis*
*Halalkalibacillus halophilus*
*Halanaerobium saccharolyticum*
*Halanaerocella petrolearia*
*Haliangium ochraceum*
*Haloanaerobium congolense*
*Haloarcula marismortui*
*Halobacillus alkaliphilus*
*Halobacillus dabanensis*
*Halobacillus halophilus*
*Halobacilus karajensis*
*Halobacillus litoralis*
*Halobacillus mangrovi*
*Halobacillus profundi*
*Hallobacillus yeomjeoni*
*Halobacter halobium*
*Halobacterium cutirubrum*
*Halobacterium halobium*
*Halobacterium noricense*
*Halobacterium salinarum*
*Halobacterium sodomense*
*Halobacterium volcanii*
*Halobacteroides halobius*
*Halochromatium glycolycum*
*Halochromatium salexigens*
*Haloferax mediterranei*
*Haloferax volcanii*
*Halogeometricum boriquense*

TABLE 1-continued

Halophillic Microorganisms

*Halogranum salarium*
*Halolactobacillus alkaliphilus*
*Halolactobacillus halophilus*
*Halomonas alkaliphila*
*Halomonas alkalitolerans*
*Halomonas boliviensis*
*Halomonas campaniensis*
*Halomonas campisalis*
*Halomonas elongata*
*Halomonas eurihalina*
*Isochromatium buderi*
*Labrys wisconsinensis*
*Lamprobacter modestohalophilus*
*Lentibacillus halodurans*
*Lentibacillus halophilus*
*Lentibacillus juripiscarius*
*Lentibacillus kapialis*
*Lentibacillus salarius*
*Lentibacillus salicampi*
*Lentibacillus salis*
*Lysinibacillus* (ex *Bacillus*) *sphaericus*
*Marichromatium fluminis*
*Marichromatium gracile*
*Marichromatium purpuratum*
*Marinococcus hispanicus*
*Mavirita roseacus*
*Methylophaga murata*
*Moritella japonica*
*Natribacillus halophilus*
*Natrinema* sp.
*Natronincola ferrireducens*
*Natrocella acetonitrilicum*
*Natrococcus occultus*
*Nitriliruptor alkaliphilus*
*Nocardiopsis aegyptia*
*Oceanobacillus iheyensis*
*Oceanobacillus kapialis*
*Oceanobacillus soja*
*Paenisporosarcina quisquiliarum*
*Paracoccus halophilus*
*Paraliobacillus quinghaiensis*
*Paraliobacillus ryukyuensis*
*Pelagibacillus goriensis*
*Piscibacillus halophilus*
*Piscibacillus salipiscarius*
*Planococcus halophilus*
*Planococcus rifietensis*
*Pontibacillus halophilus*
*Pontibacillus marinus*
*Prosthecochloris indica*
*Pseudomonas putida*
*Pseudomonas* sp.
*Psychrobacillus insolitus*
*Psychrobacillus psychrodurans*
*Psychrobacillus psychrotolerans*
*Psychrobacter salsus*
*Pyrobaculum calidifontis*
*Pyrococcus abyssi*
*Rhabdochromatium marinum*
*Rhodobaca barguzinensis*
*Salicola marasensis*
*Salicola* sp.
*Salibacillus marismortui*
*Salimicrobium hahphilum*
*Salimicrobium luteum*
*Salinibacillus aidingensis*
*Salinibacter ruber*
*Salinicoccus alkaliphilus*
*Salinicoccus salsiraiae*
*Salinicola socius*
*Salinivibrio costicola*
*Salsuginibacillus kocurii*
*Sedimenticola selenatireducens*
*Sediminibacillus halophilus*
*Shewanella algae*
*Shewanella chilikensis*
*Shewanella haliotis*
*Shewanella marina*

TABLE 1-continued

Halophillic Microorganisms

*Sporosarcina leteola*
*Stenotrophomonas* sp. D-1
*Tenuibacillus multivorans*
*Terribacillus halophilus*
*Thalassobacillus devorans*
*Thermochromatium tepidum*
*Thioalkalibacter halophilus*
*Thioalkalivibrio halophilus*
*Thioalkalivibrio versutus*
*Thiobacillus halophilus*
*Thiocapsa* sp.
*Thiococcus pfennigii*
*Thiohalocapsa halophila*
*Thiohalophilus thiocyanoxidans*
*Thiorhodococcus minor*
*Thiorhodovibrio winogradskyi*
*Virgibacillus arcticus*
*Virgibacillus halodenitrificans*
*Virgibacillus kekensis*
*Virgibacillus pantothenticus*
*Virgibacillus salinus*
*Virgibacillus sediminis*
*Virgibacillus siamensis*
*Wallemia ichthyophaga*

"Archaea" are microorganisms that perform methanogenesis, or the production of methane. In some embodiments, archaea are provided in a "mixed" culture with bacteria that perform other bioconversion steps, such as hydrolysis, acidogenesis and acetogenesis. The main biochemical processes and metabolic activities performed by the community of microbes (typically bacteria and archaea) are hydrolysis, acidogenesis, acetogenesis, and methanogenesis. If easily biodegradable substrates are used, methanogenesis is typically the rate limiting step of the overall reaction due to the lower biomass yield of archaeal strains.

"Digestion" or "bioconversion" of the substrate into a biofuel (e.g., methane, hydrogen gas, ethanol, etc.) may be carried out in accordance with procedures known in the art, for example, in batch mode, fed-batch mode, continuous mode, sequential batch reactors, etc. See, e.g., US 2011/0039321 to Tal et al.; EP 2283108; U.S. Pat. No. 4,974,106. In some embodiments, digestion may be carried out over a period of several days, e.g., over 7, 10, 14, 18, 20, 24, or 30 days. In some embodiments, the substrate may be pretreated prior to digestion in accordance with procedures taught herein or known in the art.

In some embodiments, the culture is "adapted" to the substrate, e.g., halophyte substrate, and/or saline medium. In some embodiments, the culture is adapted by exposure to the substrate and/or saline medium in a digestion reactor, such as a sequencing batch reactor (SBR). In some embodiments, the culture is exposed or cycled in the reactor once, twice, or three, four, five or more times in order to produce an adapted culture.

The term "saline", "saline solution", or "saline medium" as used herein, refers to aqueous mixtures including dissolved salts. Saline solutions include, but are not limited to, brackish water, saline water, and brine. Often the salts include NaCl, but other salts or molecules may be present and/or used to provided the desired osmotic pressure. Exemplary salts include, but are not limited to, sodium chloride, sodium sulfate, magnesium chloride, magnesium sulfate, calcium chloride, calcium sulfate, sodium bicarbonate, potassium chloride, potassium sulfate, potassium carbonate, a carbonic acid, and any combination thereof. In some embodiments of the present invention, the salt is sodium chloride.

In some embodiments, the saline medium has a salt concentration of from about 10, 15, 20, 25 or 30 g/L to about 40, 45, 50, 55, 60, 65 or 70 g/L $NaCl_{eq}$. The NaCl equivalent ("$NaCl_{eq}$") is the amount of NaCl which has the same osmotic effect as the referenced molecule. This value can be calculated with methods known in the art.

In some embodiments of the present invention, the saline medium is that found in a natural saline system such as sea and/or ocean water. Natural saline systems may range from low concentration brackish water all the way up to the solubility concentration limit of salt in aqueous systems. In some embodiments, seawater is used. In some embodiments, waste water is used. A combination of saline waters or media may also be used. In some embodiments, the process is subject to the proviso that fresh water is not added.

The term "waste water" as used herein, refers to water containing organic material, particularly aqueous waste disposed from domestic, municipal, commercial, industrial and/or agricultural uses. For example, waste water includes human and other animal biological wastes, and industrial wastes such as food processing wastewater.

The present invention is explained in greater detail in the following non-limiting Examples.

EXAMPLES

*Salicornia bigelovii* is a halophyte with tremendous potential usage as sustainable feedstock for bioenergy generation since it can be cultivated without the need for fresh water irrigation or arable land. Its oil-rich seeds can be harvested for biodiesel production with a major part of the plant remaining as *Salicornia* biomass waste (SBW) that can be anaerobically digested for biogas and nutrients recovery.

A series of biomethane potential tests (BMP) of SBW (after a mild aqueous extraction pretreatment, using salt water with 50 gNaCl/L) were conducted in different conditions and a final recovery of about 50% COD as methane from an original soluble COD concentration of 19.38 gCODs/L was obtained after 30 days with an adapted inoculum. The preliminary BMP results indicated clearly that the *Salicornia* biomass waste is, indeed, biodegradable in comparable terms to glucose with the use of an adapted inoculant.

Materials and Methods
SBW Pretreatment

All samples of *S. bigelovii* were cultivated by the International Centre for Biosaline Agriculture (ICBA) in the UAE, harvested and sun and air dried. After seed extraction, the resulting SBW was stored and ground finely using a knife mill (IKA, 10 MF Basic) prior to each extraction.

The SBW samples were subjected to aqueous extraction using a solution of 50 gNaCl/L, at 50° C., 10% (dw/v), for 1, 12 and 24 hours respectively (Chaturvedi et al., 2013). The solution was centrifuged and both the extractive supernatant (SBW-ES) and the extractive without centrifugation (SBW-E) were used as substrates of different sets of BMP.

Biomethane Potential Tests

Preliminary tests were conducted in 70 mL serum bottles with a liquid volume of 30 mL. The bottles were sealed and kept oxygen-free at the initial time. AD medium was prepared according to the literature (Angelidaki et al., 2009). The tests were carried out at 35° C. in either batch modes, of 14 days (see Table 1, setups A and B) or SBR with different cycle times (setup C).

Additional experiments (setup D) were carried in 250 mL Duran Schott™ bottles, with a liquid volume of 100 mL. The bottles were sealed and kept oxygen-free at the initial time. Experiments were carried in batch mode for 14 days. All bottles were inoculated with anaerobic digester sludge from a large wastewater treatment plant located in Mafraq, Abu Dhabi (UAE). The composition of each set of the bottles in terms of inoculum, media, and substrate proportions is detailed in Table 2.

TABLE 2

Constituents and volumes for each experiment performed per serum bottle.

|  | Setup A | Setup B | Setup C | | | Setup D |
|---|---|---|---|---|---|---|
|  |  |  | Assay | Inoc. blank | Subst. blank |  |
| Inoculum | 5 mL | 15 mL | 15 mL | — | 15 mL | 90 mL |
| Medium | 10 mL[a] | 5 mL[b] | 5 mL[b] | 5 mL[b] | 5 mL[b] | — |
| Carbon/Energy source | 10 mL | 10 mL | 10 mL | 10 mL | — | 10 mL |
| Total volume (with dil. water) | 30 mL | 30 mL | 30 mL | 30 mL | 30 mL | 100 mL |

[a]medium was prepared 3x concentrated;
[b]medium was prepared 6x concentrated.

COD, Gas Flow, as Composition Measurements

COD measurements: soluble COD concentrations in the extractives were measured via chromsulphoric acid method using commercial tests (HACH® COD cuvette test LCK 014 and LCK514, Hach Company, Loveland, Colo.). Cuvettes were read with a spectrophotometer (HACH® DR 2800, Hach Company, Loveland, Colo.).

Gas flow measurement: gas flow measurement was performed via volume displacement method. The displaced liquid was an acidic solution (pH<3) of HCl, containing 3M of NaCl, to minimize dissolved $CO_2$ and $O_2$ in solution, respectively.

Gas composition: $CH_4$ composition of the gas phase in the serum bottle headspace was measured with gas chromatography (Agilent 3000 micro GC, Agilent Technologies, Santa Clara, Calif.). Gas measurements were calibrated with standard gas mixes of known concentrations.

Results

Preliminary results on a 14-day batch test (Table 2, setup A) resulted in less than 3.5% of soluble COD conversion into $CH_4$, and only 8% conversion for the controls with glucose as sole carbon source. This was attributed to small inoculum concentrations.

A subsequent set of tests with larger amounts of inoculum (Table 2, setup B) confirmed this hypothesis with much larger methane production (FIG. 1). The different methane yields from glucose and SBW-ES initially suggested either low biodegradability or an inoculum not adapted to the SBW. A series of sequencing batch reactor (SBR) cycles were conducted to allow for biomass adaptation to the SBW (Table 2 setup C) as well as a batch test with large excess of the non-adapted inoculum (Table 2 setup D) in order to identify the true limitation factors.

Figure 2:
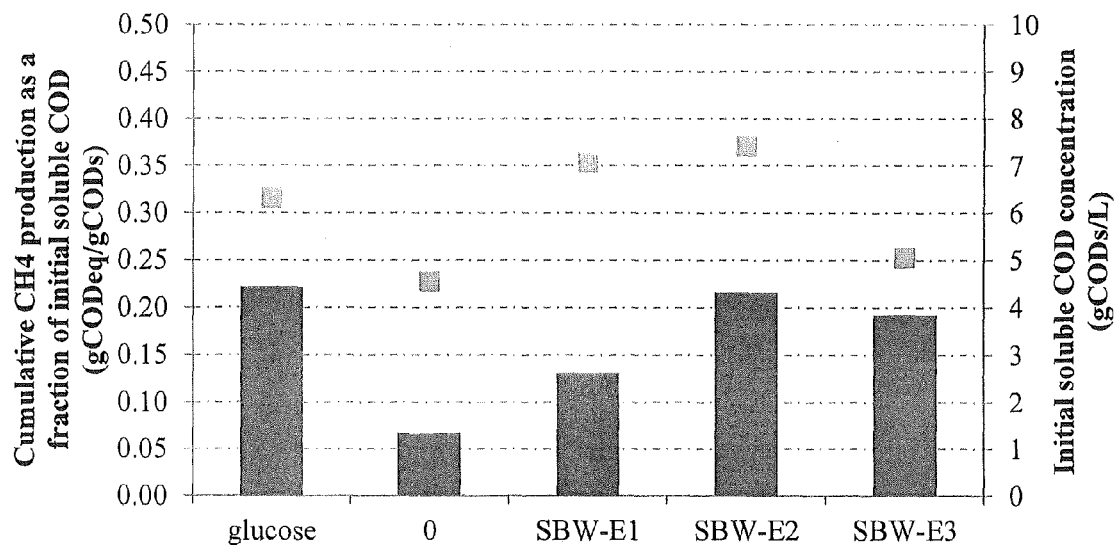
FIG. 2 shows the cumulative total methane production (from gas volume and composition) after 14-day of batch (dark grey bars), and the initial soluble COD concentration (light grey squares). SBW-E1, -E2, and -E3 are replicates. Controls with no COD source (0) and with glucose as sole COD source are shown.

The methane production results after 30 days and adapted fourth cycle SBR biomass (setup C) are presented in FIG. 1. The results for the excess inoculum test (setup D) are shown in FIG. 2.

The highest methane production values reached 54% of the initial glucose (6.3 gCODs/L) and 50% of the initial SBW (19.4 gCODs/L) (SBW-E, 24 h, 10% dw/v, 50 gNaCl/L). The presence of solids (in SBW-E fractions only) did not impact methane production. Pretreatment extraction times seemed to have minor or no impact in COD solubilization and on methane production. The very similar methane production values from SBW and glucose suggest that the true BMP of the SBW is higher, and that other non-substrate-related limitations were active during the assay.

Previous literature studies on raw halophyte biomass plants AD (including *Salicornia europaea* and others) did report times of 25-30 days and 5-10 days for mesophilic and thermophilic conditions, respectively, to achieve 80% of their final biogas (Taha et al., 2011). No data have been reported for pretreated SBW, though. The setup D assay with excess concentration of inoculum was initially planned to lower the biomethanisation times; however the non-adapted inoculum used did likely prevent better results (FIG. 2). In addition, batch mode operation is known to affect kinetics through factors such as pressurization in the bottles and accumulation of products in the medium.

Subsequent assays will use non-limiting quantities of adapted biomass inoculum and continuous operation in order to achieve the true biomethane potential of the *Salicornia* biomass waste. An overall process analysis incorporating HRT, SRT and the dilution used in the pretreatments are performed to achieve a high rate anaerobic digestion system with fastest kinetics and no inhibitions by ammonia, salinity and other possible inhibitors.

Conclusions

Biomethane potential assays with non-adapted biomass inoculum indicated that mildly pretreated *Salicornia* biomass waste (SBW) is highly biodegradable, and up to 50% of soluble COD was recovered as methane. Further adaptation of the biomass and further studies may further elucidate the true biomethane potential of the crop.

This study suggests that SBW could become a next-generation crop for biomethane and biofuels production, not requiring fresh water neither arable land.

References

Angelidaki I, Alves M, Bolzonella D, et al. 2009. Defining the biomethane potential (BMP) of solid organic wastes and energy crops: a proposed protocol for batch assays. Water Science and Technology 59(5), 927-934.

Börjesson P, Tufvesson L M. 2011. Agricultural crop-based biofuels—resource efficiency and environmental performance including direct land use changes. Journal of Cleaner Production 19(2-3):108-120, Brennan L, Owende P. 2010. Biofuels from microalgae—A review of technologies for production, processing, and extractions of biofuels and co-products. Renewable and Sustainable Energy Reviews. 14(2):557-577.

Chaturdevi T, Uratani J M, Thomsen M H, Rodríguez J. 2013. Evaluation of pre-treatment conditions on the bioavailability of biomass waste from haloagriculture of the halophyte *Salicornia bigelovii*. Proceedings of the 13th IWA World Congress on Anaerobic Digestion, Jun. 25-28, 2013, Santiago de Compostela, Spain Escobar J, Lora E S, Venturini O J, et al, 2008. Biofuels: Environment, technology and food security. Renewable and Sustainable Energy Reviews. 13(6-7):1275-1287.

Glenn, E. P., O'Leary, J. W., Watson, M. C., Thompson, T. L., Kuehl, R. O., 1991. *Salicornia bigelovii* Torr: an oil seed halophytes for sea water irrigation. Science 251, 1065-1067.

Glenn, E P., Coates, W. E., Riley, J. J, Kuehl, R. O., Swingle, R. S. 1992 *Salicornia bigelovii* Torr: A seawater irrigated forage for goats. Anim. Feed Sci Technology 40, 21-30.

Naik S N, Goud V V, Rout P K, Dalai A K. 2010. Production of first and second generation biofuels: A comprehensive review. Renewable and Sustainable Energy Reviews 14(2): 578-597.

Silva, H., Caldeira, G., Freitas, H., 2007 *Salicornia ramosissima* population dynamics and tolerance of salinity. Ecological Research 22(1),125-134.

Stoeglehner G, Narodoslawsky M. 2009. How sustainable are biofuels? Answers and further questions arising from an ecological footprint perspective. Bioresource Technology 100(16):3825-3830.

Taha F., Toderich K., Akinshina N. 2011. Promoting sustainable renewable energy production on marginal lands of Central Asia. 14th Steering Committee Meeting of the CGIAR Eco-Regional Collaborative Research Program for Central Asia and the Caucasus. Tashkent, Uzbekistan.

Warshay, B., Pan, J., Sgouridis, S. 2011 Aviation industry's quest for a sustainable fuel: considerations of scale and modal opportunity carbon benefit. Biofuels 2(1), 33-58.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties to the extent they are consistent with the description presented herein.

We claim:

1. A method for producing methane from a halophyte substrate comprising:
   providing a composition comprising said substrate in a saline medium, wherein said saline medium has a salt concentration of from about 30 g/L to about 60 g/L $NaCl_{eq}$;
   adding an adapted halophilic microbial culture to said composition in an amount effective to digest said halophyte substrate by digestion under an anaerobic condition, wherein the culture has been adapted by exposure to the halophyte substrate and saline medium in a previous fermentation and wherein said adaptation increases the yield of methane from said halophyte substrate compared to non-adapted halophilic microbial culture; and then,
   digesting said substrate with said culture for a time sufficient to produce methane therefrom, wherein said digesting is carried out in batch mode, fed-batch mode, continuous mode, or sequential batch reactors.

2. The method of claim 1, wherein at least about 50% of the total COD in the substrate is converted after 14 days of digesting said substrate in a batch mode.

3. The method of claim 1, wherein said halophyte is a *Salicornia* species.

4. The method of claim 1, wherein said halophyte is *Salicornia bigelovii*.

5. The method of claim 1, wherein the halophyte substrate is deseeded.

6. The method of claim 1, wherein the halophyte substrate consists of shoots, stems, roots, or a combination thereof, of said halophyte.

7. The method of claim 6, wherein said halophyte substrate has an ash content of 30-45% (dry weight/dry weight).

8. The method of claim 7, wherein said halophyte substrate has been dried prior to said providing step, to thereby form a dried halophyte substrate.

9. The method of claim 8, wherein the dried halophyte substrate has a total chemical oxygen demand (TCOD) of 60-80 gTCOD/100 gDM.

10. The method of claim 1, wherein said method further comprises pretreating said halophyte substrate prior to said providing step, said pretreating comprising hydrolysis of said substrate, wherein said hydrolysis is carried out in a saline solution.

11. The method of claim 10, wherein said saline solution of said pretreating step has a salinity concentration of from about 30 g/L to about 60 g/L $NaCl_{eq}$.

12. The method of claim 10, wherein said saline solution of said pretreating step comprises seawater.

13. The method of claim 10, wherein said pretreating is carried out over a time of from about 1 to about 24 hours.

14. The method of claim 10, wherein said pretreating is carried out at a temperature of from about 35 to about 95 degrees Celsius.

15. The method of claim 1, wherein said methane produced has less than about 5% hydrogen sulfide (v/v).

16. The method of claim 1, wherein said halophilic microbial culture is from a wastewater treatment plant, a marine soil sediment, a mangrove sediment, or from a combination thereof.

17. The method of claim 1, wherein said saline medium of said providing step comprises seawater, saline waste water, or a combination thereof.

18. The method of claim 1, further comprising:
   growing a halophyte plant in a saline medium, wherein said plant comprises shoots, stems, roots and seeds; and
   harvesting the seeds of said plant, wherein said harvesting is carried out by separating said seeds from said shoots, stems and roots, said remaining shoots, stems and roots forming said halophyte substrate.

19. The method of claim 1, wherein said adapted halophilic microbial culture consists of at least one halophilic species selected from the genus *Halobacterium*.

* * * * *